United States Patent [19]
Rheinheimer et al.

[11] Patent Number: 6,124,469
[45] Date of Patent: Sep. 26, 2000

[54] PROCESS FOR PREPARING SULPHUROUS 2-CHLORO-3-(4,5-DIHYDROISOXAZOL-3-YL)-BENZOIC ACIDS

[75] Inventors: Joachim Rheinheimer, Ludwigshafen; Wolfgang von Deyn, Neustadt; Joachim Gebhardt, Wachenheim; Regina Luise Hill, Speyer; Michael Rack; Hartmann König, both of Heidelberg; Norbert Götz, Worms; Volker Maywald, Ludwigshafen; Uwe Kardorff, Mannheim, all of Germany

[73] Assignee: BASF Aktiengesellschaft, Ludwigshafen, Germany

[21] Appl. No.: 09/341,519

[22] PCT Filed: Jan. 8, 1998

[86] PCT No.: PCT/EP98/00066

§ 371 Date: Jul. 13, 1999

§ 102(e) Date: Jul. 13, 1999

[87] PCT Pub. No.: WO98/31676

PCT Pub. Date: Jul. 23, 1998

[30] Foreign Application Priority Data

Jan. 17, 1997 [DE] Germany ............................ 197 01 446
Mar. 6, 1997 [DE] Germany ............................ 197 09 118

[51] Int. Cl.$^7$ .................................................. C07D 261/18
[52] U.S. Cl. ............................................................. 548/240
[58] Field of Search ............................................... 548/240

[56] References Cited

FOREIGN PATENT DOCUMENTS 245 825    11/1987    European Pat. Off. .
95/14680    6/1995    WIPO .

OTHER PUBLICATIONS

Monatsheft fur Chemie 99 (1968), pp. 815–822.

*Primary Examiner*—Deborah C. Lambkin
*Attorney, Agent, or Firm*—Keil & Weinkauf

[57] ABSTRACT

Sulfur-containing 2-chloro-3-(4,5-dihydro-3-isoxazolyl)-benzoic acids of the formula I

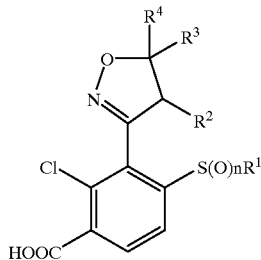

I in which the substituents have the meanings given in the description are prepared as described.

9 Claims, No Drawings

PROCESS FOR PREPARING SULPHUROUS 2-CHLORO-3-(4,5-DIHYDROISOXAZOL-3-YL)-BENZOIC ACIDS

This application is a 371 of PCT/EP98/0066 Jan. 8, 1998.

The invention relates to a process for preparing sulfur-containing 2-chloro-3-(4,5-dihydro-3-isoxazolyl)benzoic acids of the formula I

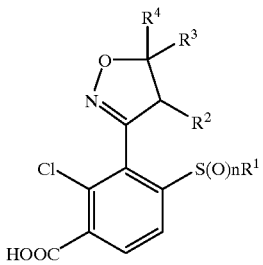

I where the substituents have the following meanings:

n 0, 1 or 2;
$R^1$ $C_1$–$C_6$-alkyl, $C_1$–$C_6$-haloalkyl;
$R^2, R^3, R^4$ hydrogen, $C_1$–$C_4$-alkyl, $C_1$–$C_4$-haloalkyl or
$R^3$ and $R^4$ together form a $C_2$–$C_6$-alkanediyl chain which may be substituted once to four times by $C_1$–$C_4$-alkyl.

The invention furthermore relates to the intermediates essential for this process: the alkylthiobenzoic acids of the formula Ia, bromo thioethers of the formula V, thioethers of the formula IV and 3-(2,6-dichlorophenyl)isoxazolines of the formula II.

WO 96/26200 has disclosed a-nine-stage process for preparing methyl 2-chloro-3-(4,5-dihydro-3-isoxazolyl)-4-methylsulfonylbenzoate in which the isoxazoline unit is assembled only toward the end of the synthetic sequence.

WO 96/26200 furthermore mentions 2,4-disubstituted 3-(heterocyclyl)benzoic acids as intermediates for herbicides. WO 95/14680 and EP-A 245 825 describe 3-phenylisoxazolines which may be substituted twice or three times in the phenyl nucleus as pharmaceuticals.

It is an object of the present invention to find a shorter route, which is less costly and can be used on an industrial scale to sulfur-containing 2-chloro-3-(4,5-dihydro-3-isoxazolyl)benzoic acids of the formula I.

We have found that this object is achieved by the process which is mentioned at the outset and which provides the required sulfur-containing 2-chloro-3-(4,5-dihydro-3-isoxazolyl)benzoic acids of the formula I in good yields (scheme 1). Alkylthiobenzoic acids of the formula Ia can thus be obtained in three stages starting from 3-(2,6-dichlorophenyl)isoxazolines of the formula II or in five stages starting from 2,6-dichlorobenzaldehyde which can be bought. An oxidation step then results in the alkylsulfonyl- or alkylsulfinylbenzoic acids of the formula Ib.

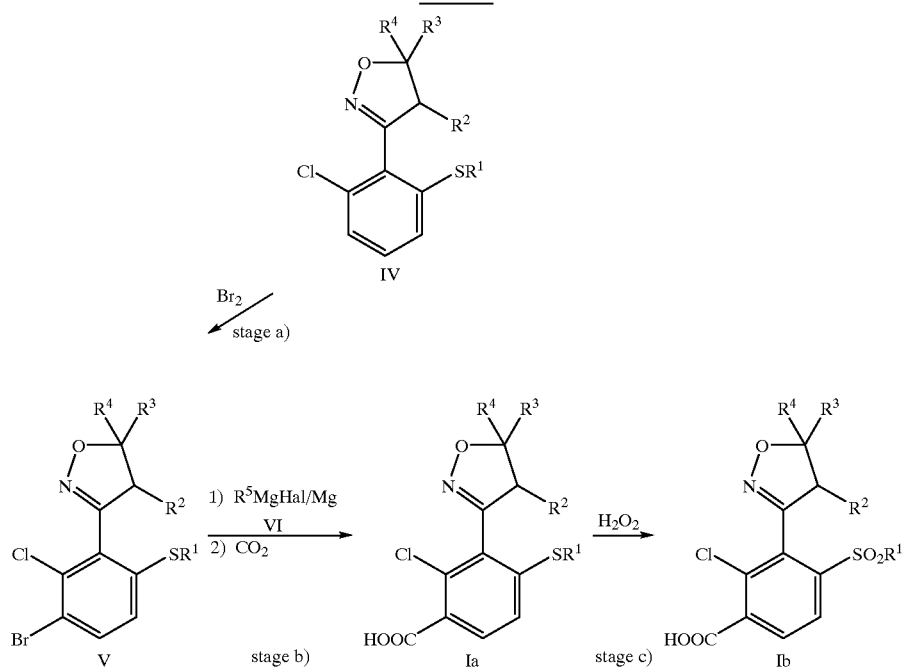

Scheme 1

The process according to the invention can be used to prepare sulfur-containing 2-chloro-3-(4,5-dihydro-3-isoxazolyl)benzoic acids of the formula I. The meanings specified above for the substituents $R^1$ to $R^4$ in formula I are collective terms for individual lists of members of individual groups. All the carbon chains, that is to say all the alkyl moieties, can be straight-chain or branched. Halogenated substituents preferably have 1–6 identical or different halogen atoms.

Examples of specific meanings are:

$C_1$–$C_4$-alkyl methyl, ethyl, n-propyl, 1-methylethyl, n-butyl, 1-methylpropyl, 2-methylpropyl and 1,1-dimethylethyl;

$C_1$–$C_6$-alkyl $C_1$–$C_4$-alkyl as specified above, plus n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-2-methylpropyl;

$C_1$–$C_6$-haloalkyl $C_1$–$C_4$-alkyl as mentioned above, which is partially or completely substituted by fluorine, chlorine and/or bromine, eg. chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, preferably trifluoromethyl.

Particularly preferred alkylthiobenzoic acids of the formula I, bromo thioethers of the formula V, thioethers of the formula IV and 3-(2,6-dichlorophenyl)isoxazolines of the formula II are those where the substituents $R^2$ to $R^4$ are each hydrogen.

The process can also, because of the reagents used and the reaction conditions, be used on an industrial scale (can be scaled up).

We have furthermore found sulfur-containing 2-chloro-3-(4,5-dihydro-3-isoxazolyl)-benzoic acids of the formula Ia, bromo thioethers of the formula V, thioethers of the formula IV and the 3-(2,6-dichlorophenyl)isoxazolines of the formula II which are suitable as intermediates.

The thioethers of the formula IV required in the process according to the invention can be prepared in various ways (scheme 2). Route C therein is particularly preferred because the thiolysis to give the thioethers IV can take place at higher temperature (0 to 120° C.) than the corresponding thiolysis reactions in processes A and B without formation of large amounts of the unwanted doubly thiolated by-product.

Scheme 2

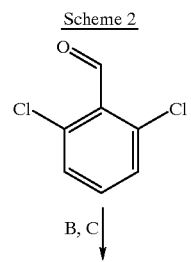

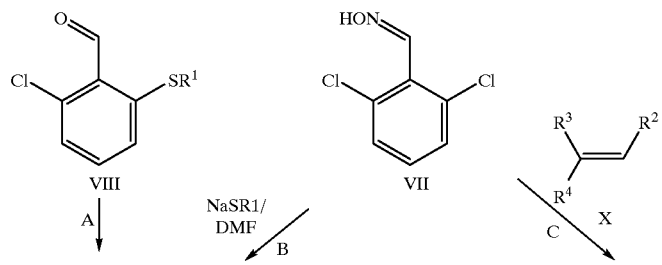

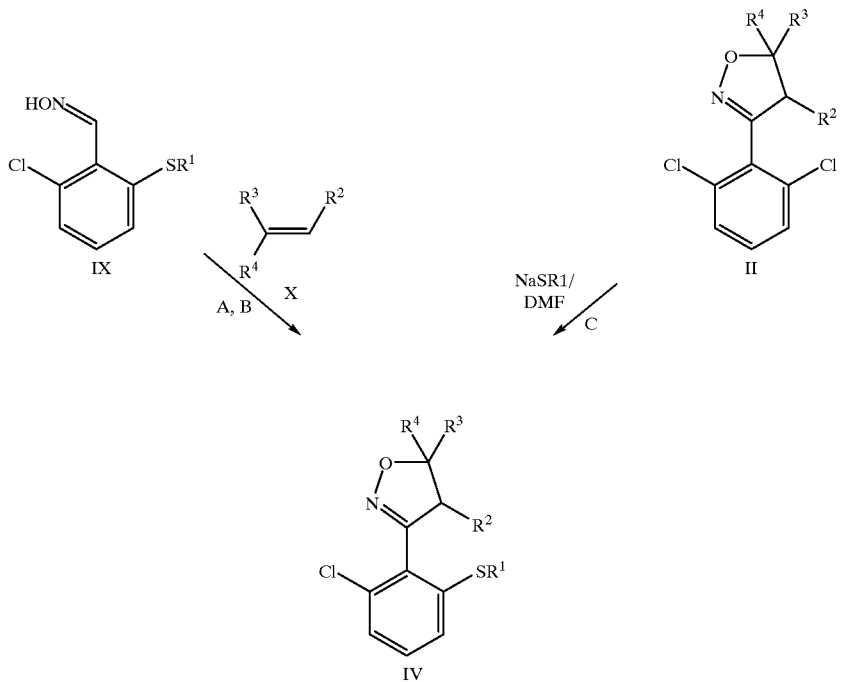

The 2,6-dichlorobenzaldoxime of the formula VII can be obtained in virtually quantitative yield by standard processes starting from 2,6-dichlorobenzaldehyde VIIa, which can be bought, by reacting with hydroxylamine in the presence of acid.

Reaction of 2,6-dichlorobenzaldoxime VII with alkenes of the formula X to give II takes place via various intermediates. Since the first reaction step is formation of an intermediate hydroximic acid halide, it is necessary for a suitable oxidizing reagent and a source of halogen or else the halogen itself to be present. The second reaction step is then elimination of hydrogen halide to give the nitrile oxide, which requires basic conditions. Thirdly and finally, the nitrile oxide undergoes cycloaddition onto the alkene.

This sequence can be carried out stepwise by conventional processes, it being possible to employ for example the free halogens bromine or chlorine to form the hydroximic acid halide. Since the hydroximic acid halides are prone to decompose, they are advantageously converted with a base into the even more sensitive nitrile oxides, which are usually trapped in situ with the alkene.

In the process according to the invention, these single steps are now advantageously combined to a one-pot reaction. This is usually carried out in a solvent, for example haloalkanes such as dichloroethane and methylene chloride or aromatic compounds such as benzene, toluene, chlorobenzene, nitrobenzene or xylene, which dissolves the organic component but does not itself interfere with the reaction. An aqueous alkali metal hypohalite solution, preferably 1–2 equivalents of commercially available sodium hypochlorite solution, is added as halogenating agent and simultaneously as base, the alkene being added in parallel or immediately thereafter. Thus the reaction mixture normally consists of two phases because the organic solvent is only incompletely miscible with the alkali metal hypohalite solution. For complete conversion, it may be advantageous to add 3–50% sodium or potassium acetate, but this is not absolutely necessary.

Gaseous alkenes of the formula X are passed in, while liquid alkenes are appropriately metered in. The alkenes are usually employed in a molar ratio of from 1 to 5:1 relative to the oxime VII.

The reaction is generally carried out at from 0 to 80° C., preferably from 20 to 50° C.

The thiolysis of the resulting 3-(2,6-dichlorophenyl) isoxazolines II is carried out with a thiol of the formula III $R^1SH$   III, but preferably with its alkali metal salt IIIa.

In place of IIIa it is also usually possible to employ the thiol III with the addition of bases such as alkali metal or alkaline earth metal carbonates, alkali metal or alkaline earth metal hydroxides or alkali metal alcoholates. It is often possible by adding copper powder as catalyst (0.01–10 mol %) to speed up and complete the conversion.

Polar solvents have proven suitable for this reaction. Polar aprotic solvents such as dimethylformamide, dimethylacetamide, N-methylpyrrolidone, dimethylpropyleneurea and tetramethylurea are particularly preferred.

The thiolysis is usually carried out at from 0 to 100° C., preferably at 20–50° C.

The procedures for the individual stages in routes A and B can be similar to the relevant ones in route C. It should merely be noted that thiolysis of 2,6-dichlorobenzaldehyde to VIII (route A) should usually take place at from −30 to 30° C., preferably from −20 to 0° C., and thiolysis of VIIb to IX (route B) should take place at from −10 to 80° C., preferably 0 to 60° C.

Brominating agents suitable for the bromination of the thioethers IV to the bromo thioethers V are elemental bromine, NBS and dibromodimethylhydantoin.

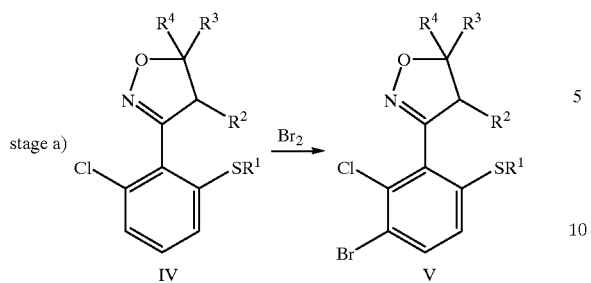

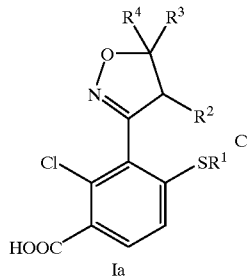

Elemental bromine in the presence of concentrated sulfuric acid has proven particularly suitable. It is in fact possible in this case to introduce both bromine atoms into the product. It is normal to use from 0.5 to 0.7 equivalent, preferably 0.5 to 0.6 equivalent, of bromine.

Brominations in concentrated sulfuric acid have to date been described only for deactivated derivatives which are, however, stable to acid and hydrolysis, such as dinitrobenzene (Monatsh. für Chem. 99 (1968), 815–22). However, the thioethers VI have, with the thioether and isoxazoline moieties, two moieties which are sensitive to oxidation and hydrolysis, respectively. Nevertheless, surprisingly, the reaction takes place chemoselectively. Thus, when the reaction is carried out suitably, less than 5% of by-products such as the corresponding sulfoxide or hydrolysis products are formed.

The reaction is usually carried out at from −10 to 80° C., preferably at 0 to 50° C.

It is possible to add as catalyst for example sulfur, iodine or dibromodimethylhydantoin, but this is not normally necessary.

It is also possible to use other solvents as alternatives to sulfuric acid, for example $C_1$–$C_4$-carboxylic acids and, of these, in particular acetic acid.

Considerable amounts of heat are liberated during the hydrolytic workup of the bromination which has been carried out in concentrated sulfuric acid. Nevertheless, the reaction mixture should be kept below 80° C., preferably below 50° C., during the workup in order to prevent possible side reactions as far as possible.

Carboxylation of the bromo thioethers V to give the alkylthiobenzoic acids of the formula Ia takes place via the corresponding intermediate aryl Grignard compounds. The aryl Grignard compounds are formed by reacting the bromo thioethers V with magnesium or with an alkyl Grignard compound of the formula VI, where $R^5$ is $C_1$–$C_6$-alkyl and Hal is chlorine, bromine or iodine. Particularly preferred for this purpose is isopropylmagnesium chloride.

The aryl Grignard compound is formed selectively at the position of the bromine atom. Side reactions indicating the intermediate formation of an aryne, because of the neighboring chlorine atom, have not been observed. On the other hand, alkylsulfonyl radicals are not inert to Grignard reagents under the chosen reaction conditions. It therefore proves to be another advantageous aspect of the process according to the invention that, to prepare the sulfoxides and sulfones of the formula Ib, the alkylsulfonyl unit is assembled only after the carboxyl group.

To prepare the arylmagnesium compound it is possible to dispense partly or completely with the alkylmagnesium compound of the formula VI and to employ in its place magnesium powder.

If only magnesium powder is used, it can first be activated by one of the methods disclosed in the literature (Organikum, 1993 Barth Verlagsgesellschaft Leipzig, page 518), with isopropyl chloride or isopropyl bromide being particularly suitable. Another preferred possibility for activating the magnesium powder is to add from 0.1 to 30, preferably 3 to 15, mol % of an isopropylmagnesium chloride solution to the powder.

Magnesium powder is generally employed in a molar ratio of from 0.9 to 2 relative to the bromo thioether V; the alkylmagnesium compounds of the formula VI in a molar ratio of from 0.9 to 3, preferably 1.0 to 2.0.

The reaction is carried out in solvents which are inert under the reaction conditions. Ethers are particularly preferred, such as tetrahydrofuran, diethyl ether, dimethoxyethane or methyl tert-butyl ether. As a rule, the reaction is carried out at from −10 to 80° C. and preferably from 10 to 60° C.

The carboxylation reaction is usually carried out by adding gaseous or solid carbon dioxide in a molar ratio of from 1 to 10 relative to the bromo thioether V employed.

The oxidation of the alkylthiobenzoic acids Ia to the corresponding alkylsulfonyl- or alkylsulfinylbenzoic acids of the formula Ib is preferably carried out with hydrogen peroxide, the sulfoxides being obtained with approximately equivalent amounts of oxidant, and the sulfones being obtained with about double the molar quantities.

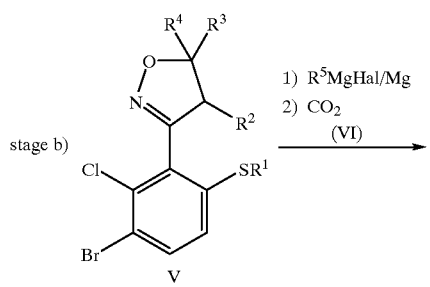

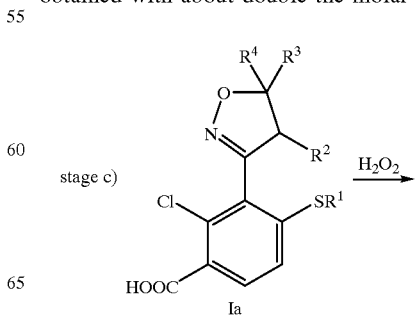

-continued

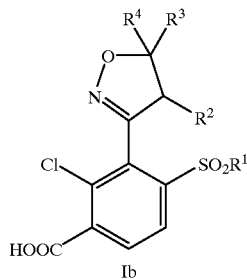

Ib

Solvents which can be used are water, acetonitrile, carboxylic acids such as acetic acid, trifluoroacetic acid, propionic acid, alcohols such as methanol, ethanol, isopropanol, tert-butanol, chlorinated hydrocarbons such as methylene chloride, 1,1,2,2-tetrachloroethane or ketones such as acetone or methyl ethyl ketone. Water, methanol, acetic acid and trifluoroacetic acid are particularly preferred.

In a particularly preferred variant, the reaction can also be catalyzed by adding relatively strong acids such as trifluoroacetic acid or perchloric acid. However, metal compounds are also suitable as catalysts, eg. transition metal oxides such as vanadium pentoxide, sodium tungstate, potassium dichromate, iron oxide tungstate, sodium tungstate/molybdic acid, osmic acid, titanium trichloride, selenium dioxide, phenylselenenic acid, vanadyl 2,4-pentanedionate.

The catalysts are generally employed in an amount of from 0.5 to 10%, but it is also possible to employ stoichiometric amounts because the inorganic catalysts can easily be filtered off and recovered.

Another preferred oxidizing agent is peracetic acid or hydrogen peroxide/acetic anhydride, possibly also the peracetic acid which is present in equilibrium in a hydrogen peroxide/acetic acid mixture.

A preferred oxidizing agent is also pertrifluoroacetic acid or the hydrogen peroxide/trifluoroacetic acid mixture or else the hydrogen peroxide/trifluoroacetic anhydride mixture.

Oxidation with hydrogen peroxide in glacial acetic acid is generally very selective, but frequently slow. The reaction time can generally be reduced by adding trifluoroacetic acid.

It is possible furthermore to use as solvents petroleum ether, the abovementioned solvents and the abovementioned catalysts.

Besides peracetic acid and pertrifluoroacetic acid, it is also possible to employ perbenzoic acid, monoperphthalic acid or 3-chloroperbenzoic acid, expediently in chlorinated hydrocarbons such as methylene chloride or 1,2-dichloroethane.

Also very suitable for oxidizing the thiols to sulfoxides or sulfones are chlorine and bromine. Favorable solvents are water, acetonitrile, dioxane, two-phase systems such as aqueous potassium bicarbonate solution/dichloromethane, and acetic acid.

It is furthermore possible to employ as source of active halogen tert-butyl hypochlorite, hypochlorous and hypobromous acids, their salts, also N-halo compounds such as N-bromo- and N-chlorosuccinimide or else sulfuryl chloride.

Also favorable for the oxidation are dinitrogen tetroxide, eg. in the technically simple variant with air/nitrogen dioxide or trioxide and, for example, osmium(VIII) oxide as catalyst. The oxidation can also be carried out directly with nitric acid, in which case suitable additional solvents are acetic anhydride and acetic acid, and suitable catalysts are copper(I) and (II) bromide and chloride.

Also suitable for the oxidation is photosensitized oxygen transfer, in which case recommended photosensitizers are chlorophyll, protoporphyrin, rose bengal or methylene blue. Suitable inert solvents are hydrocarbons such as pentane, hexane, heptane, cyclohexane, chlorinated hydrocarbons such as methylene chloride, 1,2-dichloroethane, 1,1,2,2-tetrachloroethane, alcohols such as methanol, ethanol, n-propanol or isopropanol, ketones such as acetone, methyl ethyl ketone, polar aprotic solvents such as acetonitrile, propionitrile or aromatic hydrocarbons such as benzene, toluene, chlorobenzene or xylene. In place of oxygen, it is also possible to use ozone in the abovementioned solvents, plus ether, 1,4-dioxane or THF.

Besides photosensitization, catalysts are also advisable for oxidation with oxygen, eg. oxides and sulfides of nickel, copper, aluminum, tungsten, chromium, vanadium, ruthenium, titanium, manganese, molybdenum, magnesium and iron.

Either sulfoxides or sulfones Ib are obtained depending on the stoichiometry of the oxidizing agents used. The molar ratios in which the starting compounds are reacted together are generally 0.9–1.8, preferably 1.05–1.3, for the ratio of alkylthiobenzoic acid Ia to oxidizing agent in the case of oxidation to alkylsulfinylbenzoic acid Ib (m=0) and generally 1.9–3.5, preferably 2.05–2.9 in the case of oxidation to alkylsulfonylbenzoic acid Ib (m=1).

The concentration of the precursors in the solvent is generally 0.1–5 mol/l, preferably 0.2–2 mol/l.

It is advantageous to introduce the alkylthiobenzoic acid with one of the abovementioned catalysts into one of the abovementioned solvents and then to add the oxidizing agent over the course of 0.25–20 hours with stirring.

The oxidations can be carried out under atmospheric or superatmospheric pressure, continuously or batchwise.

The alkylthiobenzoic acids Ia according to the invention and the alkylsulfonylbenzoic acids Ib obtainable therefrom are valuable precursors for preparing crop protection agents, especially herbicides, as described in WO 96/26200, WO 96/26192, WO 96/26193 and WO 96/26206.

The process according to the invention is presented below by means of examples.

Preparation of Starting Materials

EXAMPLE 1

Preparation of 2-chloro-6-methylthiobenzaldehyde 20.0 g (0.114 mol) of 2,6-dichlorobenzaldehyde were dissolved in 100 ml of dimethylformamide and, while stirring at −15° C. under nitrogen protective gas, 7.54 g (0.107 mol) of sodium methanethiolate were added. The mixture was stirred at −10 to −15° C. for 5 h and then at room temperature for 12 h. The mixture was taken up in methyl tert-butyl ether, washed with water, dried over sodium sulfate and concentrated under reduced pressure. Yield 19.6 g (92%) of solid.

Purity: >95% (NMR, GC). $^1$H-NMR (CDCl$_3$, ppm): δ=2.47 (s); 7.23 (m); 7.44 (t); 10.66 (s).

The melting point measured on a sample purified by chromatography on silica gel was 82° C.

EXAMPLE 2

Preparation of 2-chloro-6-methylthiobenzaldoxime 69.2 g (0.371 mol) of 2-chloro-6-methylthiobenzaldehyde were dissolved in 500 ml of methanol and, at room temperature, 93.5 g (1.11 mol) of sodium bicarbonate and 91.3 g (0.557 mol) of hydroxylammonium sulfate were added. The mixture was stirred at room temperature for 12 h, filtered to remove insolubles and concentrated under reduced pressure. The residue was taken up in methyl tert-butyl ether, washed with water, dried over sodium sulfate and concentrated under reduced pressure. Yield 69.0 g (92.3%) of solid of melting point 143° C.

Purity: >95% (NMR). $^1$H-NMR (CDCl$_3$, ppm): δ=2.47 (s); 7.10–7.30 (m); 8.58 (s); 8.67 (s).

EXAMPLE 3

Preparation of 2,6-dichlorobenzaldoxime 50.0 g (0.286 mol) of 2,6-dichlorobenzaldehyde were added to 250 ml of tetrahydrofuran and 250 ml of water, and 26.0 g (0.159 mol) of hydroxylammonium sulfate were added. The mixture was then stirred at 40° C. for 3 h, keeping the pH at 4–5 by adding sodium bicarbonate solution. The tetrahydrofuran was then distilled off under reduced pressure, and the residue was extracted with methyl tert-butyl ether, and the solution was dried over sodium sulfate and concentrated under reduced pressure. Yield 54.3 g (99.9%) of solid of melting point 150° C.

Purity: >97% (NMR). $^1$H-NMR (CDCl$_3$, ppm): δ=7.20–7.40 (m); 8.42 (s); 9.10 (br.).

Preparation of 3-(2,6-dichlorophenyl)isoxazolines of the formula II

EXAMPLE 4

Preparation of 3-(2,6-dichlorophenyl)-4,5-dihydroisoxazole a) 10.0 g (52.6 mmol) of 2,6-dichlorobenzaldoxime were suspended in 150 ml of dichloromethane. After the introduction of ethylene had started, 32.7 g (64.3 mmol) of 12% strengthسsodium hypochlorite solution to which a spatula tip of sodium acetate had been added were added dropwise at 15–20° C. After the addition was complete, the mixture was warmed to 26–30° C. and ethylene was passed in for a further 6 h. The organic phase was then separated off, washed with water, dried over sodium sulfate and concentrated under reduced pressure. Final weight 10.5 g (92.4%) of solid of melting point 100–101° C. Purity 99.0% (GC). $^1$H-NMR (CDCl$_3$): δ=3.31 (t); 4.56 (t); 7.25–7.45 (m).

A similar experiment with 20.8 g of 2,6-dichlorobenzaldoxime resulted in a yield of 93% with a purity of 99.2% (GC).

b) 31.4 g (0.165 mol) of 2,6-dichlorobenzaldoxime were suspended in 350 ml of 1,2-dichlorethane. At room temperature, 103 ml (0.202 mol) of 12% strength sodium hypochlorite solution were added, during which the mixture warmed up to 45° C. Ethylene was then passed in for 2 h at the reflux temperature, a spatula tip of sodium acetate was added, and ethylene was again passed in for 2 h. The organic phase was separated off, dried over sodium sulfate and concentrated under reduced pressure. Final weight 31.6 g (88.7%) of solid. Purity 98.2% (GC).

c) Starting from 2,6-dichlorobenzaldehyde 75 g (0.43 mol) of 2,6-dichlorobenzaldehyde were dissolved in 400 ml of toluene and then 155 g (0.24 mol) of 25% strength hydroxylammonium sulfate solution were added. At 75° C., 38 g of 50% strength NaOH were added dropwise.

After stirring for half an hour, the phases were separated at 75° C., and the organic phase was washed with water and then cooled. At 25° C., 276 g (0.46 mol) of 12.5% strength sodium hypochlorite solution were added dropwise over 4–6 h while simultaneously passing in ethylene. After addition of the hypochlorite solution was complete, the mixture was stirred for 1 h, the phases were separated, the organic phase was washed with water, and the solvent was distilled off under reduced pressure. 82 g (89% of theory) of the required product were obtained with a purity (by GC) of 96%.

Preparation of thioethers of the Formula IV

EXAMPLE 5

Preparation of 3-(2-chloro-6-methylthiophenyl)-4,5-dihydroisoxazole a) Starting from 2-chloro-6-methylthiobenzaldoxime 57.5 g (0.285 mol) of 2-chloro-6-methylthiobenzaldoxime were suspended in 600 ml of dichlormethane. After introduction of ethylene had started, 180 ml (0.354 mol) of 12% strength hypochlorite solution were added dropwise at 20–25° C. After the addition was complete, the mixture was warmed to 33° C., and ethylene was passed in for a further 5 h. Then 2 spatula tips of sodium acetate were added and ethylene was passed in for a further 30 min. The organic phase was then separated off, washed with water, dried over sodium sulfate and concentrated under reduced pressure. Final weight 59.2 g (91%) of yellowish solid of melting point 62–64° C. Purity 90% (NMR). Yield: (weight×purity) about 81%. $^1$H-NMR (CDCl$_3$): δ=2.45 (s); 3.33 (t); 4.55 (t); 7.15–7.35 (m).

b) Starting from 3-(2,6-dichlorophenyl)-4,5-dihydroisoxazole 0.68 g (9.72 mmol) of sodium methanethiolate was added to 2.0 g (9.26 mmol) of 3-(2,6-dichlorophenyl)-4,5-dihydroisoxazole dissolved in 20 ml of dimethylformamide at room temperature, and the mixture was stirred at 35° C. for 3 h. It was then diluted with methyl tert-butyl ether, washed with water, dried over sodium sulfate and concentrated under reduced pressure. Final weight 2.1 g (99.7%). GC showed 88.7% product and 9.4% starting material present.

bb) 200 g (0.93 mol) of 3-(2,6-dichlorophenyl)-4,5-dihydroisoxazole were dissolved in 620 ml of N-methylpyrrolidone. The apparatus was evacuated (100–20 mbar) and then, at 60–65° C., 330 g (1.02 mol) of 21% strength methanolic thiomethoxide solution were introduced while distilling off the methanol. After the methanol distillation was complete, the mixture was stirred for 1 h and then diluted with 1.8 l of water and extracted with toluene. The organic phase was washed with water and then the toluene was distilled off under reduced pressure. Recrystallization from isopropanol resulted in 169 g (80% of theory) of required product with a purity (by GC) of 95%.

EXAMPLE 6

Preparation of 2-chloro-3-(4,5-dihydro-3-isoxazolyl)-4-methylsulfonylbenzoic acid Stage a:
Preparation of 3-(3-bromo-2-chloro-6-methylthiophenyl)-4,5-dihydroisoxazole a) 1.54 g (9.6 mmol) of bromine were slowly added dropwise at room temperature to 4.0 g (17.6 mmol) to 3-(2- chloro-6-methylthiophenyl)-4,5-dihydroisoxazole dissolved in 30 ml of concentrated sulfuric acid, during which the mixture warmed up slightly. It was then stirred for 1 h and, after cooling to 0° C., 200 ml of ice-water were cautiously added over the course of 30 min, keeping the temperature below 25° C. Subsequent stirring for 15 minutes was followed by extraction with ethyl acetate, and the organic phase was washed with water, dried over sodium sulfate and concentrated under reduced pressure. Yield 4.45 g (82.6%) of solid. Purity >95% (GC). $^1$H-NMR (CDCl$_3$): δ=2.45 (s); 3.30 (t); 4.58 (t); 7.05 (d); 7.63 (d).

aa) 45.0 g (0.198 mol) of 3-(2-chloro-6-methylthiophenyl)-4,5-dihydroisoxazole were dissolved in 310 ml of concentrated sulfuric acid at 5° C. Then 17.42 g (109 mmol) of bromine were added over the course of 3 min, during which the mixture warmed up to 8° C. It was stirred at 0–5° C. for 1.5 h and at room temperature for 45 min, cooled to 0° C. and slowly stirred into 2 l of ice-water. The oily solid which separated out was removed, washed with 400 ml of sodium bicarbonate solution and 150 ml of water and dried under reduced pressure. Final weight 34.3 g (56.6%), melting point 92–93° C., purity 98% (GC), also present are 1.4% starting material and 0.6% sulfoxide.

The aqueous phase was extracted with methyl tert-butyl ether, and the extracts were dried over sodium sulfate and concentrated under reduced pressure. Yield 23.9 g (39.4%), melting point 89–90° C., purity 94.9% (GC), also present are 2.0% of starting material and 3.1% sulfoxide.

Taking the purity of the two fractions into account, this corresponds to an isolated yield of 93%.

Stage b:
Preparation of 2-chloro-3-(4,5-dihydroisoxazol-3-yl)-4-methylthiobenzoic acid b) Under nitrogen, 19.0 ml (38.0 mmol) of a 2 molar solution of isopropylmagnesium chloride in tetrahydrofuran were added dropwise to 9.3 g (30.3 mmol) of 3-(3-bromo-2-chloro-6-methylthiophenyl)-4,5-dihydroisoxazole dissolved in 75 ml of tetrahydrofuran at room temperature. During this, the mixture warmed up to 40° C. It was then stirred at room temperature for 2 h, 20 g of dry ice were added in portions, during which the temperature fell to 10° C., and the mixture was acidifed to pH 0–1 with 10% strength hydrochloric acid, keeping the temperature below 20° C. by external cooling. Subsequently 20 ml of concentrated brine were added, and extraction with ethyl acetate was followed by drying over sodium sulfate and concentration under reduced pressure. Yield 8.2 g of solid. Purity about 80% ($^1$H-NMR). For purification, a sample of 0.66 g was dissolved in 15 ml of 15% strength sodium hydroxide solution, washed with 10 ml of methylene chloride and acidified to pH 0–1 with concentrated hydrochloric acid, and the product was filtered off and dried under reduced pressure. Yield 0.45 g (68%) of white solid of melting point 198–200° C. Purity >95% ($^1$H-NMR). Calculated for the complete batch, this corresponds to an isolated yield of about 68%. $^1$H-NMR (DMSO-d$_6$, ppm): δ=2.53 (s); 3.25 (t); 4.48 (t); 7.43 (d); 7.87 (d); 13.4 (broad).

bb) 8.3 kg (342 mol) of magnesium were dried at 60° C. under 100 mbar for 1.5 h. 14 l of tetrahydrofuran were added and the reaction was started at 60° C. with 500 ml of 1,2-dibromoethane. The contents of the vessel started to boil. Then 24.3 kg (310 mol) of isopropyl chloride in 128 l of tetrahydrofuran were added over the course of 2 hours with evaporative cooling. After the addition was complete, the mixture was refluxed for 8 hours. It was then cooled to 10° C. under nitrogen. A solution of 79.2 kg (258 mol) of 3-(3-bromo-2-chloro-6-methylthiophenyl)-4,5-dihydroisoxazole dissolved in 215 l of tetrahydrofuran was metered in with cooling at 10–26° C. over the course of 2 hours. The mixture was then stirred at 20–25° C. for 35 minutes. Subsequently, 23 kg of carbon dioxide (523 mol) were passed in at −7 to 0° C. over the course of 3.5 hours, and stirring was continued at ambient temperature overnight. The reaction mixture was hydrolyzed by adding it over the course of 30 minutes to a solution of 42 l of 31% strength hydrochloric acid in 172 l of water at 10–26° C. Then 225 l of tetrahydrofuran were distilled off under atmospheric pressure up to an internal temperature of 67° C. The mixture was subsequently cooled to 60° C., and 380 l of water were added to precipitate the product. The remaining tetrahydrofuran (160 l) was distilled off under 500 mbar up to an internal temperature of 78° C. The reaction mixture was cooled to 20° C. and filtered. The product was washed with 100 l of water and then dried at 50° C. with 3 bar of nitrogen. Yield: 61 kg (87%) of pale brown solid. Purity: >96% (HPLC).

bbb) Experiment with magnesium powder and isopropylmagnesium chloride 0.6 ml (1.2 mmol) of a 2 molar solution of isopropylmagnesium chloride in tetrahydrofuran and 0.6 ml of tetrahydrofuran were added to 235 mg (9.79 mmol) of magnesium powder (270 mesh) under nitrogen in an oven-dried glass flask. The temperature rose to 33° C. during this. Then 1 ml of tetrahydrofuran and 1 ml of a solution of 2.5 g (8.16 mmol) of 3-(3-bromo-2-chloro-6-methylthiophenyl)-4,5-dihydroisoxazole in 12 ml of tetrahydrofuran (solution A) were added. The temperature rose briefly to 37° C. during this. The mixture was warmed to 39° C., and a further 4 ml of solution A were added dropwise. After stirring for 15 min, the temperature had fallen to 31° C., and the remaining solution A and 3 ml of tetrahydrofuran were added. After 15 min the mixture was warmed to 42° C. and stirred at this temperature for 30 min. About 4 g of dry ice were added, during which the temperature fell to −10° C., and the mixture was stirred for 10 min and acidified to pH 0–1 with 10% strength hydrochloric acid, keeping the temperature below 40° C. by external cooling. Then 10 ml of concentrated brine were added and, after extraction with ethyl acetate, the combined extracts were washed with water, dried over sodium sulfate and concentrated under reduced pressure. Yield 2.21 g of solid, purity about 75–80% ($^1$H-NMR). Yield (weight×purity) about 75–80%.

Stage c:
Preparation of 2-chloro-3-(4,5-dihydro-3-isoxazolyl)-4-methylsulfonylbenzoic acid c) 200 l of 30% strength hydrogen peroxide (1854 mol) were added over the course of 5 hours to 167 kg of 2-chloro-3-(4,5-dihydro-3-isoxazolyl)-4-methylthiobenzoic acid (616 mol) and 5.0 kg of sodium tungstate hydrate (15 mol) in 260 l of glacial acetic acid at 59° C. The reaction mixture warmed up to 66° C. during this and was kept at this temperature by external cooling. After the addition was complete, the mixture was stirred at 60–65° C. for 4 hours. Then 113 l of water were added at 65° C., and the mixture was slowly cooled to 10° C. (5° C./h) and stirred at 10–15° C. overnight. The contents of the vessel were filtered off, washed with water, predried under an elevated nitrogen pressure, and dried in an oven at 60° C. (100 mbar). Yield: 170 kg (90.9%) of colorless solid of melting point 145–146° C. The substance is pure according to $^1$H-NMR and immediately suitable for synthesis of active substances.

$^1$H-NMR (DMSO-$d_6$, ppm): δ=1.92 (s, acetic acid); 3.30 (s), 3.33 (t); 4.52 (t); 8.07 (m); 12.3 (br.).

EXAMPLE 7

Preparation of 2-chloro-3-(4,5-dihydro-3-isoxazolyl)-4-methyl-sulfonylbenzoic acid (one-pot variant: stage b and c)

A solution of 27.6 g (0.09 mol) of 3-(3-bromo-2-chloro-6-methylthiophenyl)-4,5-dihydroisoxazole in 75 ml of tetrahydrofuran was added dropwise over the course of 10 minutes to 50 ml of a 2.0 M isopropylmagnesium chloride solution in tetrahydrofuran at 20–25° C., followed by stirring for 30 minutes. At −5 to 5° C., 5 g (0.114 mol) of carbon dioxide were passed in over the course of 30 minutes. Then, at 20–26° C., 209.7 g of a 12% strength sodium hypochlorite solution were added dropwise over the course of 80 minutes, followed by stirring for 3.5 hours. A mixture of 12.5 ml of conc. hydrochloric acid and 62.5 ml of water was added over the course of 10 minutes to result in two clear phases. The aqueous phase was separated off and extracted with 80 ml of tetrahydrofuran. The two organic phases were combined. The remaining tetrahydrofuran was then removed and replaced by water under atmospheric pressure up to an external temperature of 100° C. The reaction mixture was cooled to room temperature to precipitate the product. Finally, it was washed with water and dried. Yield: 24.2 g (86%) of white solid. Purity: >97% (HPLC).

We claim:

1. A process for preparing sulfur-containing 2-chloro-3-(4,5-dihydro-3-isoxazolyl)benzoic acids of the formula Ia or Ib

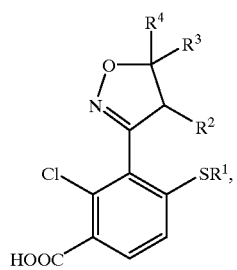

Ia

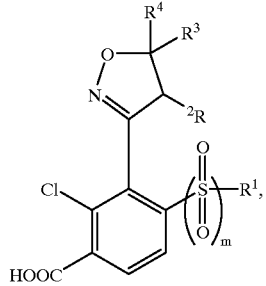

Ib where the substituents have the following meanings:

m is 0 or 1;

$R^1$ $C_1$–$C_6$-alkyl, $C_1$–$C_6$-haloalkyl;

$R^2$,$R^3$,$R^4$ hydrogen, $C_1$–$C_4$-alkyl, $C_1$–$C_4$-haloalkyl or $R^3$ and $R^4$ together form a $C_2$–$C_6$-alkanediyl chain which may be substituted once to four times by $C_1$–$C_4$-alkyl, which comprises a) brominating a thioether of the formula IV

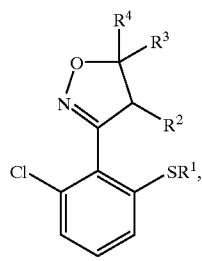

IV where $R^1$ to $R^4$ have the abovementioned meanings, with a brominating agent to give the bromo thioether of the formula V

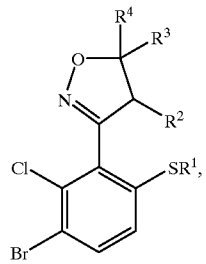

V where $R^1$ to $R^4$ have the abovementioned meanings, and reacting the bromo thioether V b) with magnesium powder and/or a Grignard compound of the formula VI $R^5$Mg—Hal    VI, where Hal is Cl, Br or I and $R^5$ is $C_1$–$C_6$-alkyl, in the presence of carbon dioxide to give alkylthiobenzoic acids of the formula Ia

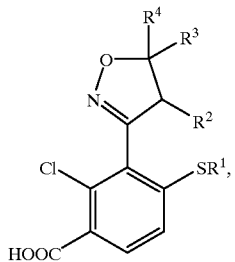

Ia where $R^1$ to $R^4$ have the abovementioned meanings, and to prepare compounds Ib then, optionally c) oxidizing with an oxidizing agent to the corresponding alkylsulfonyl and alkylsulfinylbenzoic acids of the formula Ib

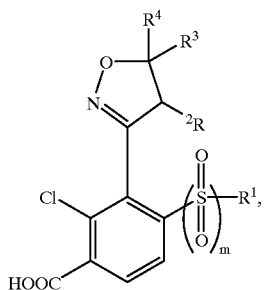

Ib where $R^1$ to $R^4$ have the abovementioned meanings, and m can be 0 or 1.

2. A process for preparing thioethers of the formula IV as set forth in claim 1, which comprises reacting 2,6-dichlorobenzaldehyde with a thiol of the formula III

  III, where $R^1$ has the meaning given in claim 1, in the presence or absence of a base, to give the thioether of the formula VIII

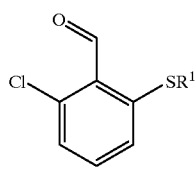

VIII and then converting thioether VIII with hydroxylamine into the oxime IX

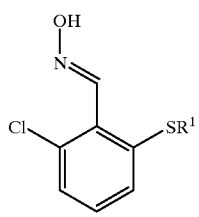

IX which is finally reacted with an alkene of the formula X

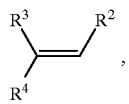

X where $R^2$ to $R^4$ have the meanings stated in claim 1, in the presence of a suitable oxidizing agent.

3. A process for preparing thioethers of the formula IV as set S forth in claim 1, which comprises reacting the oxime of the formula VII

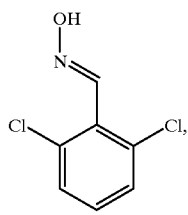

VII with a thiol of the formula III to give the oxime IX, and finally reacting oxime IX with an alkene of the formula X in the presence of a suitable oxidizing agent.

4. A process for preparing thioethers of the formula IV as set forth in claim 1, which comprises reacting the oxime of the formula VII with an alkene of the formula X in the presence of a suitable oxidizing agent to give 3-(2,6-dichlorophenyl)-isoxazoline of the formula II

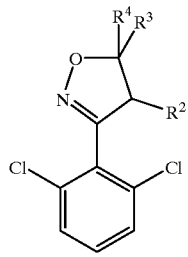

II and reacting compound II with a thiol of the formula III in a solvent.

5. A process as claimed in claim 1, wherein the reaction in stage a) is carried out with elemental bromine in concentrated sulfuric acid at from −10 to 80° C.

6. A process as claimed in claim 1, wherein in stage b) the solution of a bromo thioether of the formula V is reacted in an ethereal solvent with a suspension of from 0 to 2 equivalents of magnesium and/or from 0.05 to 1.2 equivalents of a Grignard compound of the formula VI at from 0 to 50° C., and the intermediate aryl Grignard compound is reacted with at least one equivalent of carbon dioxide.

7. A process as claimed in claim 1, wherein hydrogen peroxide is employed as oxidizing agent in stage c).

8. An alkylthiobenzoic acid of the formula Ia

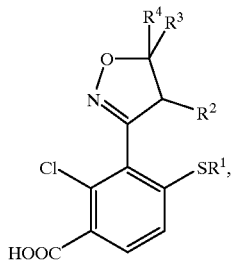

Ia where the substituents have the following meanings:

$R^1$ $C_1$–$C_6$-alkyl, $C_1$–$C_6$-haloalkyl;

$R^2$,$R^3$,$R^4$ hydrogen, $C_1$–$C_4$-alkyl, $C_1$–$C_4$-haloalkyl or $R^3$ and $R^4$ together form a $C_2$–$C_6$-alkanediyl chain which may be substituted once to four times by $C_1$–$C_4$-alkyl.

9. A bromo thioether of the formula V

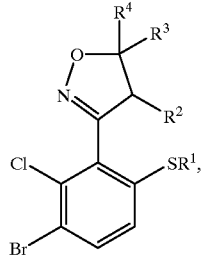

V where $R^1$ to $R^4$ have the meanings as defined in claim 1.

* * * * *

UNITED STATES PATENT AND TRADEMARK OFFICE
CERTIFICATE OF CORRECTION

PATENT NO.: 6,124,469

DATED: September 26, 2000

INVENTOR(S): RHEINHEIMER et al.

It is certified that error appears in the above-identified patent and that said Letters Patent is hereby corrected as shown below:

Col. 18, claim 3, line 23, delete "S".

Signed and Sealed this

Twenty-second Day of May, 2001

*Attest:*

NICHOLAS P. GODICI

*Attesting Officer*  Acting Director of the United States Patent and Trademark Office